(12) United States Patent
Spiegel

(10) Patent No.: US 11,156,507 B2
(45) Date of Patent: Oct. 26, 2021

(54) METHOD AND DEVICE FOR DETECTING THE TEMPERATURE OF THE VIBRATING ELEMENT OF AN ULTRASONIC CONVERTER

(71) Applicant: Elmos Semiconductor AG, Dortmund (DE)

(72) Inventor: Egbert Spiegel, Marl (DE)

(73) Assignee: ELMOS SEMICONDUCTOR SE, Dortmund (DE)

( * ) Notice: Subject to any disclaimer, the term of this patent is extended or adjusted under 35 U.S.C. 154(b) by 433 days.

(21) Appl. No.: 16/264,914

(22) Filed: Feb. 1, 2019

(65) Prior Publication Data
US 2019/0242761 A1    Aug. 8, 2019

(30) Foreign Application Priority Data
Feb. 5, 2018 (DE) ............... 10 2018 102 535.1

(51) Int. Cl.
*G01K 11/22* (2006.01)
*G01K 11/26* (2006.01)
*G10K 11/02* (2006.01)
*G01H 11/04* (2006.01)
*G01K 7/20* (2006.01)
*A61B 8/00* (2006.01)
*G01K 7/34* (2006.01)
(Continued)

(52) U.S. Cl.
CPC ............. *G01K 11/26* (2013.01); *A61B 8/546* (2013.01); *G01H 11/04* (2013.01); *G01K 7/203* (2013.01); *G01K 7/34* (2013.01); *G10K 11/02* (2013.01); *B06B 1/06* (2013.01); *G01H 13/00* (2013.01); *G01K 2217/00* (2013.01);

(58) Field of Classification Search
USPC .......................................... 374/117, 119, 100
See application file for complete search history.

(56) References Cited

U.S. PATENT DOCUMENTS

| 2011/0228809 A1* | 9/2011 | Tadigadapa | G01K 7/32 374/31 |
| 2016/0252406 A1* | 9/2016 | Sherrit | H03H 9/17 374/117 |
| 2018/0224385 A1* | 8/2018 | Magee | B06B 1/0644 |

FOREIGN PATENT DOCUMENTS

| CH | 625881 A5 | 10/1981 |
| DE | 69130843 T2 | 6/1999 |

(Continued)

*Primary Examiner* — Mirellys Jagan
(74) *Attorney, Agent, or Firm* — Mindful IP PLLC

(57) ABSTRACT

Disclosed is a method for detecting a value which represents the temperature of a vibrating element of an ultrasonic transducer. The ultrasonic transducer has a resonant frequency ($f_r$). The method comprises the steps of operating the ultrasonic transducer with an electric measuring signal at a measuring frequency ($f_m$) which is above the resonant frequency, and of detecting the absolute value of the complex impedance of the ultrasonic transducer at this measuring frequency ($f_m$) and, building thereon, ascertaining the desired value, which is to represent the temperature of a vibrating element of an ultrasonic transducer, as a function of the detected absolute value of the complex impedance of the ultrasonic transducer at this measuring frequency ($f_m$).

20 Claims, 14 Drawing Sheets

(51) Int. Cl.
*G01H 13/00* (2006.01)
*B06B 1/06* (2006.01)

(56) References Cited

FOREIGN PATENT DOCUMENTS

DE 19917372 B4 1/2009
EP 0463735 B1 2/1999

* cited by examiner

METHOD AND DEVICE FOR DETECTING THE TEMPERATURE OF THE VIBRATING ELEMENT OF AN ULTRASONIC CONVERTER

CROSS-REFERENCE TO RELATED APPLICATIONS

This application claims priority to German Patent Application Number 10 2018 102 535.1 filed on Feb. 5, 2018, the content of which is incorporated herewith by reference in its entirety.

TECHNICAL FIELD

The disclosure relates to a method and to a device for detecting the temperature of the vibrating element of an ultrasonic converter, and in particular of an ultrasonic transducer.

BACKGROUND

When it comes to ultrasonic sensor systems, knowledge about the ambient temperature is advantageous in the following respects:
for specifying the absolute value of the speed of sound as a function of the temperature necessary, for example, for ascertaining the propagation time (temperature coefficient of approximately 1750 ppm/K);
for controlling the transmission frequency of the ultrasonic converter since the resonant frequency decreases as the temperature increases (temperature coefficient of approximately −300 ppm/K to −400 ppm/K).

The expression "x ppm/K" shall mean that, proceeding from a reference value ref at the reference temperature (for example, 20° C.), the particular parameter (here, the speed of sound or the resonant frequency, for example) changes by $\times 10^{-6}$ per ° C.

Knowing the temperature of the diaphragm (which is to say of the vibrating element) of the ultrasonic transducer is helpful for controlling the transmission frequency. Knowing the temperature of the outside air is helpful for calculating the propagation time. For the sake of simplicity, however, the temperature used is typically the chip temperature of the controlling semiconductor circuit. From a technical perspective, it would be better to use a separate temperature sensor outside the controlling semiconductor circuit so as to reduce the distortion caused by self-heating as a result of the operation of the circuit. The ultrasonic converter itself, however, offers the best thermal coupling to the outside air, and more specifically in automotive applications in particular, such as parking assistance systems in which the ultrasonic sensor system is arranged on the bumper.

A measuring device for detecting the temperature and the vibrations of a surface is known from DE-A-199 17 372, which is provided with a sensing tip to be placed on the surface to be measured, a vibration sensor for detecting the vibrations of the sensing tip, and a temperature sensor for detecting the temperature of the sensing tip.

DE-T-691 30 843 (EP-B-0 463 735) describes a piezoelectric temperature sensor.

CH-A-625 881 discloses a temperature measuring system comprising temperature-sensitive resonators for high voltage transformers.

SUMMARY

It is the object of the disclosure to create a solution that allows the temperature of the vibrating element of an ultrasonic converter, and in particular of an ultrasonic transducer, to be measured, and more specifically without additional sensor system hardware.

To achieve this object, according to the disclosure a method for ascertaining the temperature of the vibrating element of an ultrasonic converter, and in particular of an ultrasonic transducer, having a resonant frequency is used, wherein in the method:
the ultrasonic converter is operated with an electric measuring signal having a frequency ($f_m$) that is at least 0.2 times or at least 0.3 times or at least 0.4 times or at least 0.5 times or at least 0.6 times or at least 0.7 times the resonant frequency ($f_r$) greater or smaller than the resonant frequency ($f_r$);
the complex impedance of the ultrasonic converter is ascertained upon activation by way of the measuring signal having this frequency, and the absolute value of the complex impedance is determined; and
based on the level of the absolute value of the complex impedance and the frequency of the measuring signal for the operation of the ultrasonic converter, the temperature of the vibrating element of the ultrasonic converter is ascertained.

According to the disclosure, furthermore a device for ascertaining the temperature of the vibrating element of an ultrasonic converter having a resonant frequency is also used to achieve the object, comprising:
a measuring device for providing a measuring signal for at least partially activating the ultrasonic converter with a frequency that is at least 0.2 times or at least 0.3 times or at least 0.4 times or at least 0.5 times or at least 0.6 times or at least 0.7 times the resonant frequency ($f_r$) greater or smaller than the resonant frequency ($f_r$);
wherein the level of the complex impedance of the ultrasonic converter arising upon activation of the ultrasonic converter with a measuring signal having one of the aforementioned frequencies, and the absolute value thereof, can be ascertained by way of the measuring device; and
an evaluation unit for ascertaining the temperature of the vibrating element of the ultrasonic converter based on the level of the absolute value of the complex impedance and the frequency of the measuring signal.

Finally, the above object is also achieved by the use of the above method according to the disclosure or the use of the above device according to the disclosure for
adapting the temperature-dependent propagation time of the sound waves emitted by the ultrasonic converter to the current temperature of the vibrating element in connection with the ascertainment of the distance of an object reflecting the sound waves in the surrounding area of the ultrasonic converter and/or
adapting the frequency of the operating signal of the ultrasonic converter for exciting the vibrating element of the ultrasonic converter at the temperature-dependent resonant frequency.

Correspondingly, the disclosure thus provides to ascertain the temperature of the vibrating element of the ultrasonic converter based on the level of the absolute value of the complex impedance and based on the frequency of the measuring signal. As an essential feature of disclosure, it must be noted that the measuring signal frequency is different from the resonant frequency of the ultrasonic converter. According to the disclosure, the measuring frequency deviates by at least 0.2 times the resonant frequency from the same, whereby the following applies to the measuring frequency:

$f_m \geq f_r(1+0.2)$ or $f_m \leq f_r(1-0.2)$.

The finding that the parallel capacitance of the electrical equivalent circuit of the ultrasonic converter is the determinative element of the ultrasonic converter for the electrical properties is essential for the determination of the measuring frequency. The equivalent circuit of an ultrasonic converter essentially comprises a series connection composed of an inductor, a capacitor and a resistor. The aforementioned parallel capacitance is parallel to this series connection. This will be described in greater detail hereafter in connection with an example based on FIG. 1.

In a further advantageous example, it may be provided that the dependence of the temperature of the vibrating element on the level of the absolute value of the complex impedance of the ultrasonic converter is determined in advance, with the frequency of the measuring signal as a parameter, and in particular stored in a look-up table of the evaluation unit, and that the temperature of the vibrating element of the ultrasonic converter can be ascertained with the aid of this relationship based on the level of the absolute value of the complex impedance and the frequency of the measuring signal during operation of the ultrasonic converter.

In a further advantageous example, it may be provided that the relationship for any possible frequency of the measuring signal as a parameter is an essentially linear mapping of the reciprocal value of the level of the absolute value of the complex impedance of the ultrasonic converter against the temperature of the vibrating element.

In a further advantageous example, it may be provided that the temperature of the vibrating element of the ultrasonic converter is ascertained in the form of a value representing this temperature.

In a further advantageous example, it may be provided that the vibrating element comprises a piezoelectric element.

BRIEF DESCRIPTION OF THE DRAWINGS

The disclosure will be described in more detail hereinafter based on the drawings. In the drawings in detail.

DESCRIPTION

Figure 1:
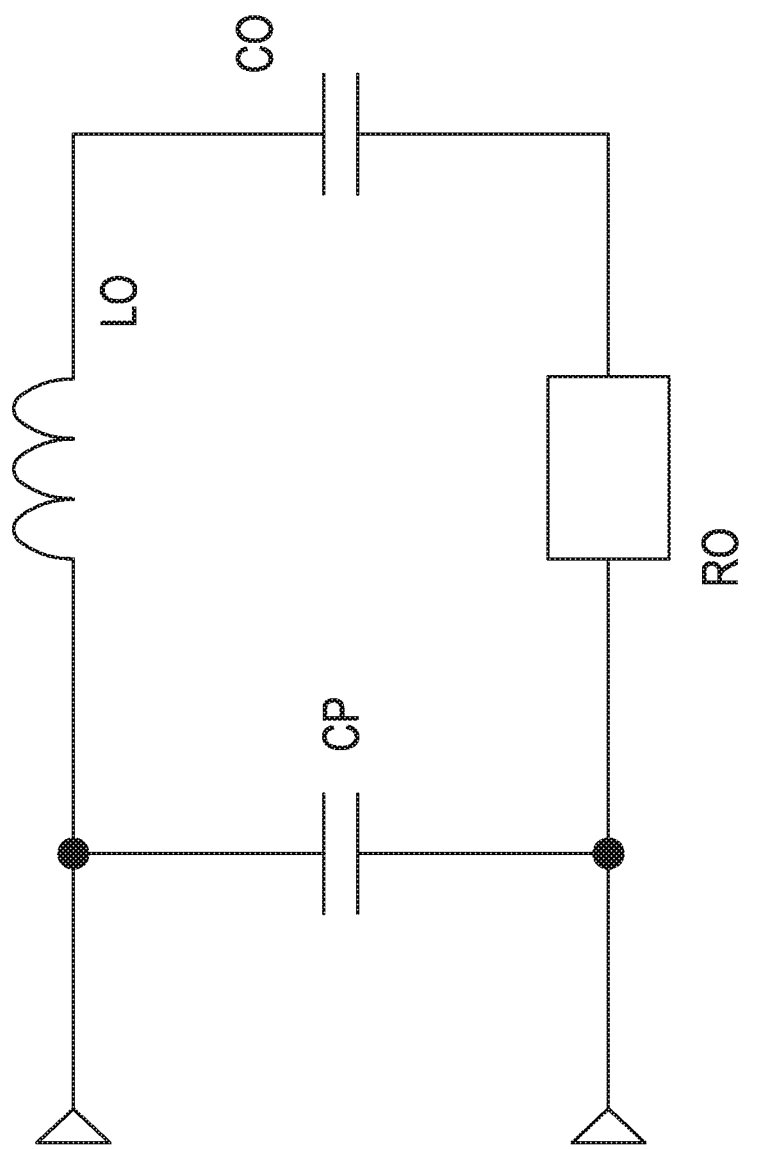
FIG. 1 shows the electrical equivalent circuit of an ultrasonic converted, and in particular of an ultrasonic transducer, designed in this case with a piezoelectric element as the vibrating element.

The examination of ultrasonic transducers (installed in particular in self-contained buildings) has shown that the electrical components of the equivalent circuit of such an ultrasonic transducer determining impedance exhibit a strong temperature dependence and can thus always be used as temperature sensors. Reference shall be made to FIG. 1 at this point.

In the equivalent circuit of FIG. 1, CP represents the parallel capacitance of the piezoelectric element, which is the vibrating element of the ultrasonic transducer. The resonant circuit represents the mechanical behavior. L0 is the series inductance of the series oscillating circuit in the equivalent circuit of the ultrasonic transducer. C0 is the series capacitance in the series oscillating circuit in the equivalent circuit of the ultrasonic transducer. R0 is the series resistance in the series oscillating circuit in the equivalent circuit of the ultrasonic transducer.

FIGS. 2 to 5, by way of example, show the typical behavior of these equivalent components as a function of the temperature (indicated in ° C.).

Figure 2:
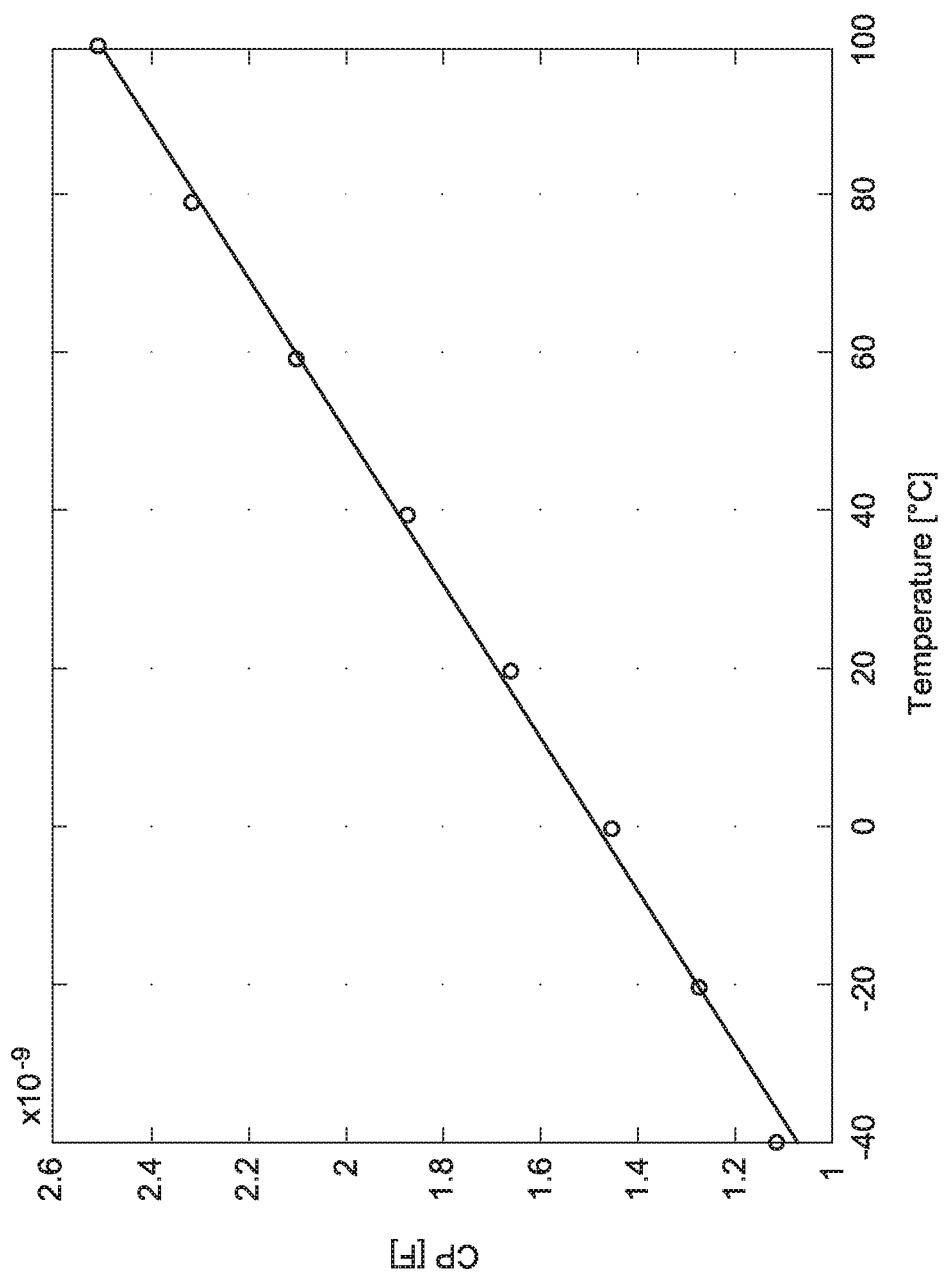
FIGS. 2 to 5 show graphical representations of the typically encountered temperature behavior of the equivalent components (components of the electrical equivalent circuit) of the ultrasonic converter according to FIG. 1.

FIG. 2 shows the exemplary value of the parallel capacitance (CP) of the piezoelectric element as a function of the temperature with a linear regression line. The slope of this regression line is 6120 ppm/K, for example (which corresponds to the temperature coefficient of the parallel capacitance (CP)).

Figure 3:
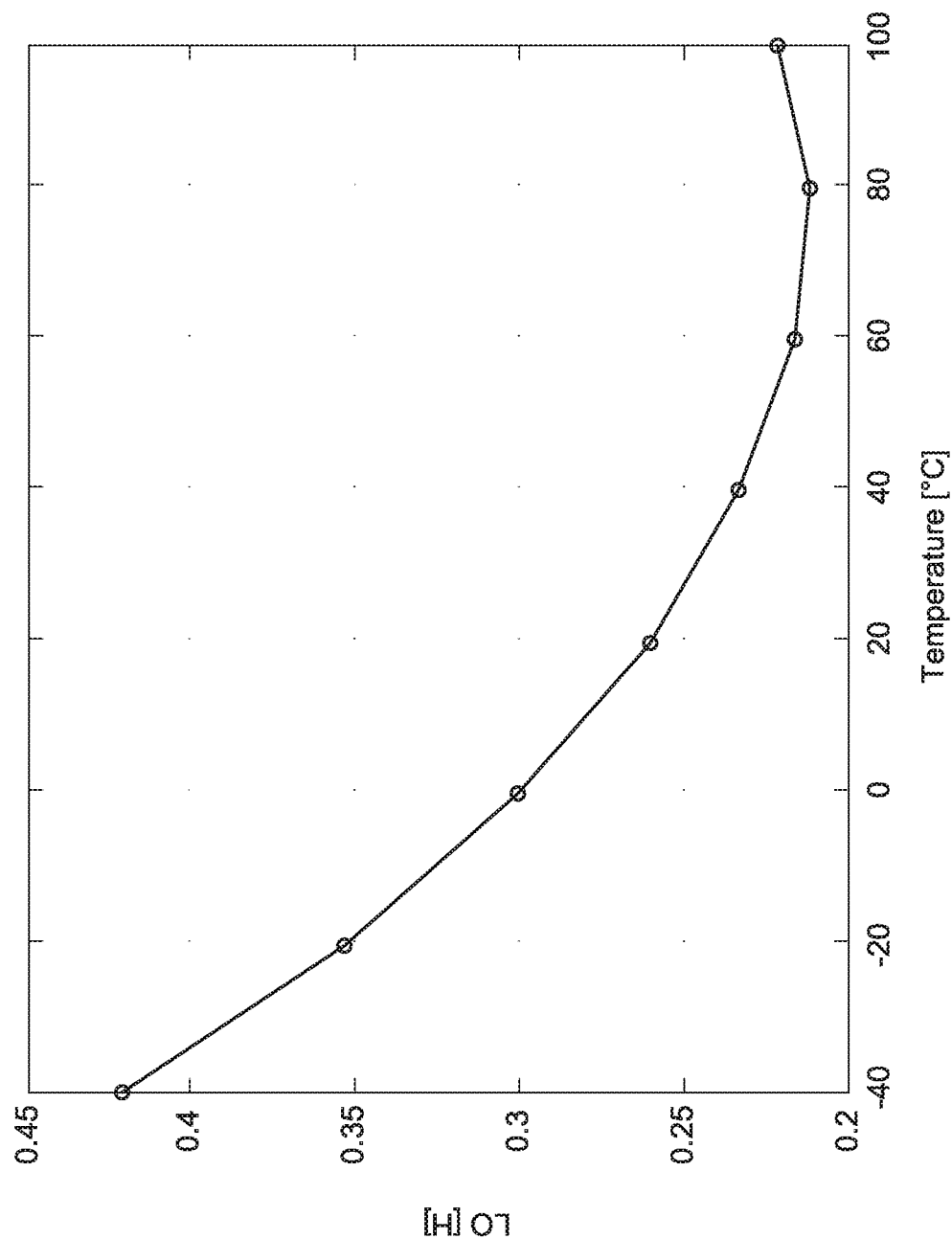

FIG. 3, by way of example, shows the change in the value of the series inductance L0 in the series oscillating circuit in the equivalent circuit of the ultrasonic transducer as a function of the temperature.

Figure 4:
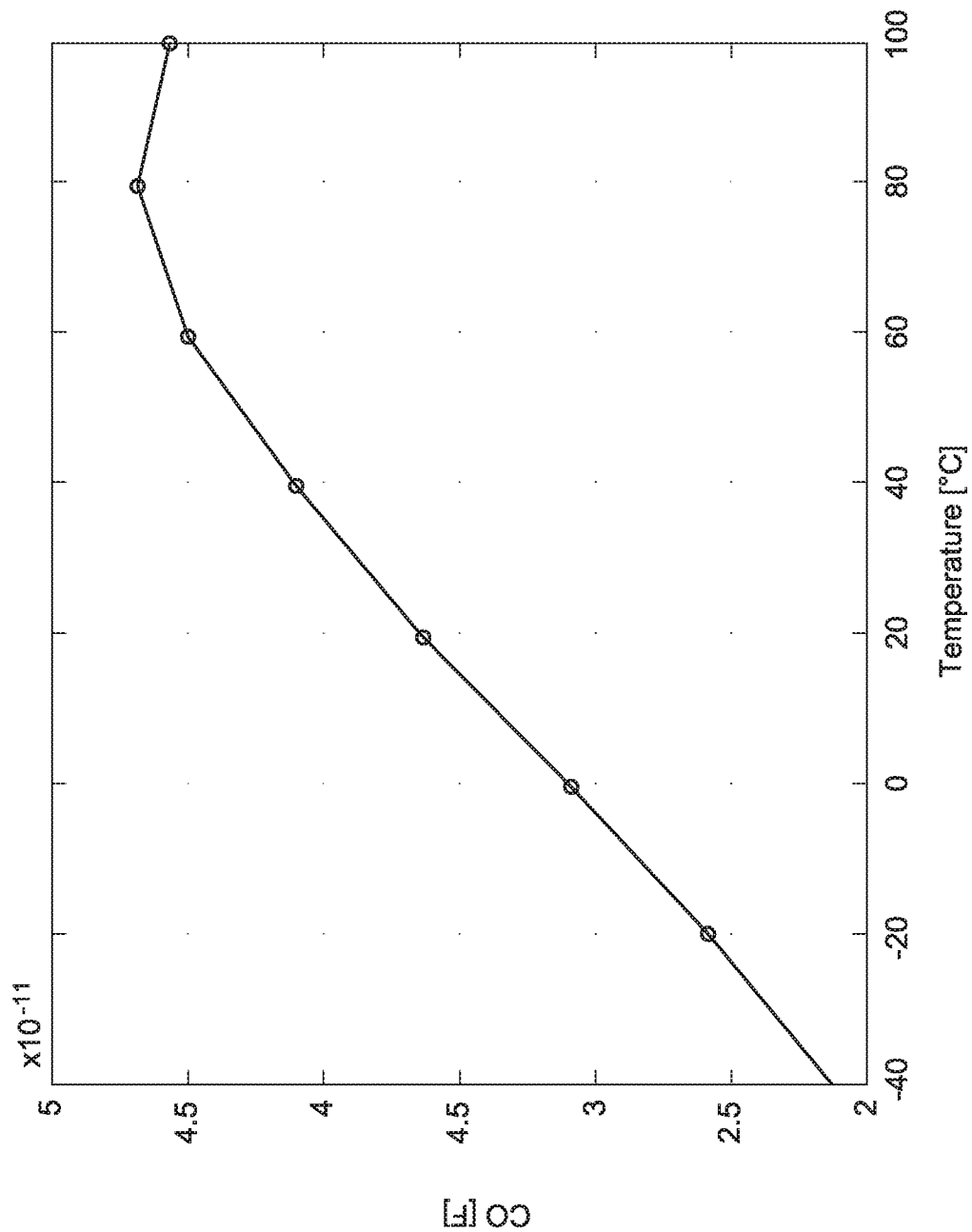

FIG. 4, by way of example, shows the change in the value of the series capacitance C0 in the series oscillating circuit in the equivalent circuit of the ultrasonic transducer as a function of the temperature.

Figure 5:
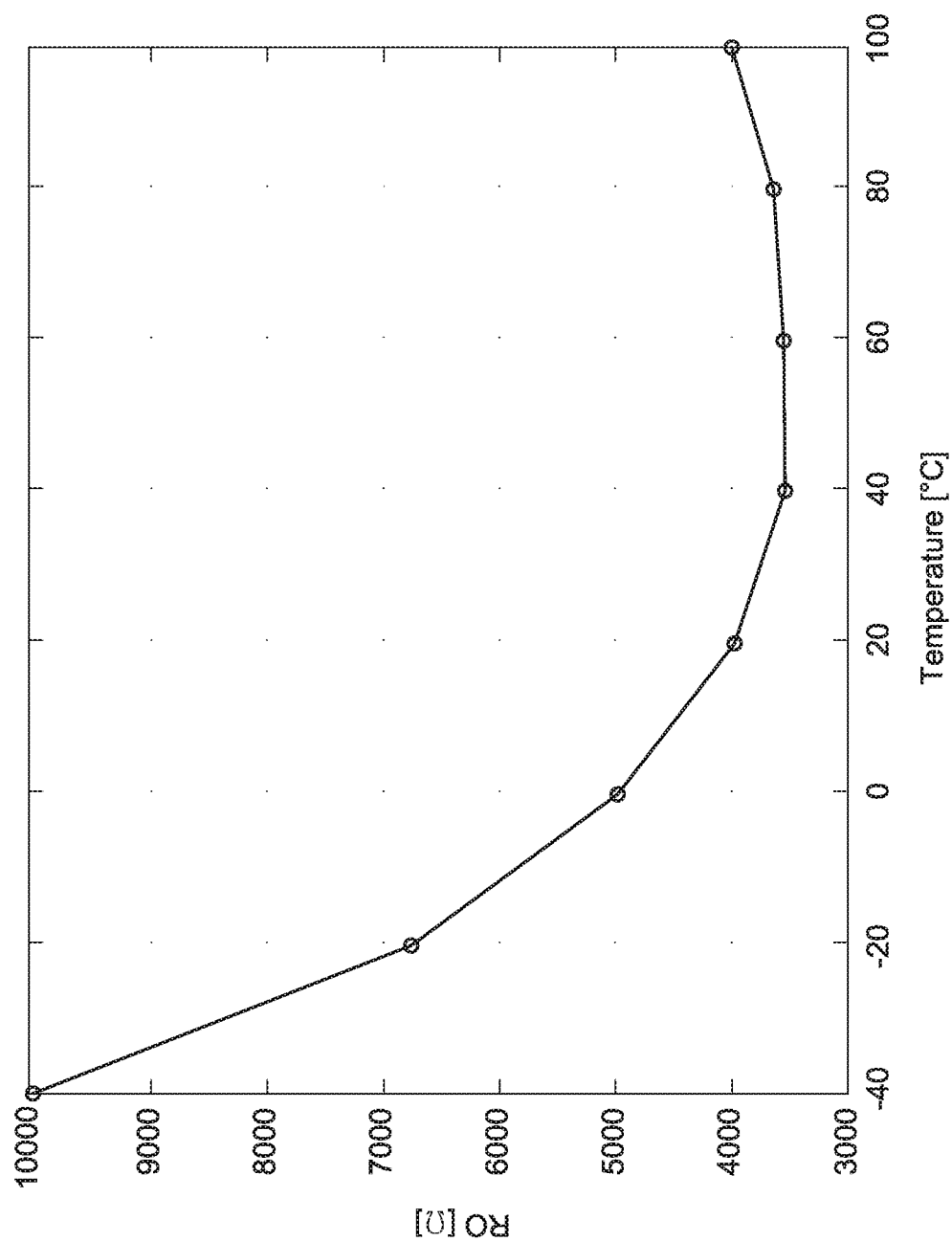

FIG. 5, by way of example, shows the change in the value of the series resistance R0 in the series oscillating circuit in the equivalent circuit of the ultrasonic transducer as a function of the temperature.

With the exception of the parallel capacitance CP, the components of the series oscillating circuit (C0, L0, R0) exhibit strong non-linear temperature dependencies. Additionally, these components (C0, R0, L0) are subject to larger production spreads, which during production cannot be readily directly controlled. Only the resonant frequency $$f_r = \frac{1}{2\pi\sqrt{L0 * C0}}$$

and the sound pressure are generally subjected to production control. The capacitance is usually specified with a maximum of +/−20% in the data sheets.

Figure 6:
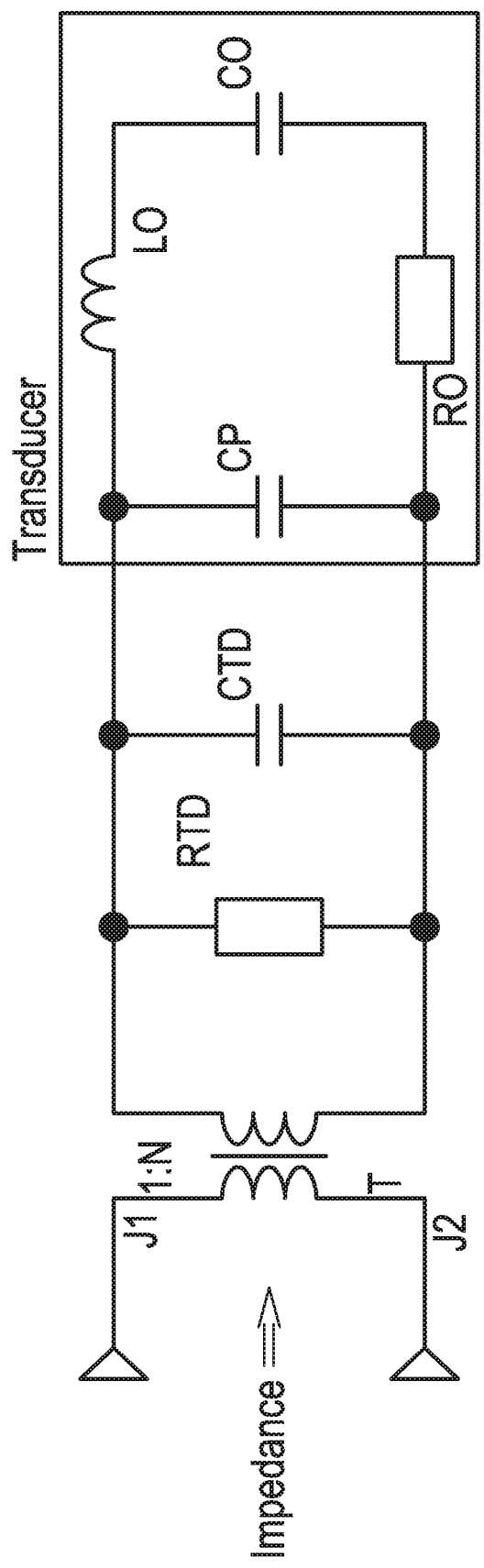
FIG. 6 shows the circuit diagram for a temperature measuring application using an ultrasonic converter.

Based thereon, it shall now be demonstrated how the temperature behavior of the capacitance can be determined using impedance measurement. FIG. 6 shows the interconnection of the ultrasonic transducer in the measuring application for the temperature determination.

Figure 7:
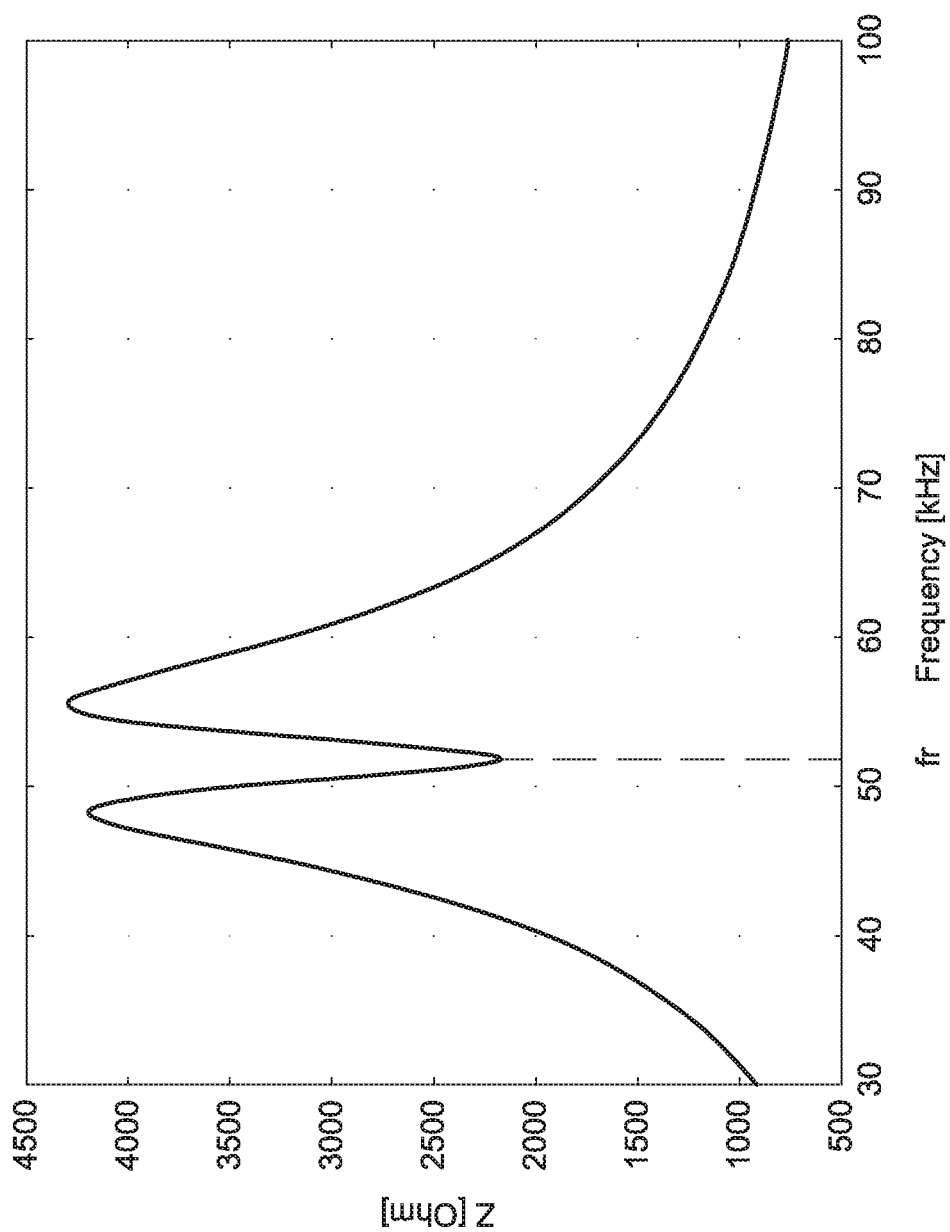
FIG. 7 shows the absolute value of the complex impedance of the ultrasonic converter as a function of the measuring signal frequency.

So as to generate the high voltage required during operation of the ultrasonic transducer during a transmission process, the activation takes place by way of a transformer having the transformer inductance (LT). The additional capacitance (CTD) is used to smooth the parallel capacitance (CP) of the ultrasonic transducer, so that the resonant frequency ($f_r$) of the parallel resonant circuit, composed of the transformer inductance (LT) and the parallel circuit made up of the parallel capacitance (CP) and the additional capacitance (CP), has a lesser response to temperature changes. This parallel resonant circuit is preferably set, by calculation, to the same resonant frequency as the series resonant circuit of the ultrasonic transducer made up of the series resistor (R0), series inductor (L0) and series capacitor (C0). The additional resistance (RTD) is used to optimize the settling time of the ultrasonic transducer after the completion of the transmission process. The impedance measurement can take place without further connections and external components via the connections of the activation circuit by way of a measuring current, detecting a measuring voltage. FIG. 7 shows the result of such a measurement in the form of a simulation.

FIG. 7 shows the change in the absolute value of the complex impedance of the transducer with circuiting as a function of the signal frequency with which the measurement is carried out. The caving notch in the center of the maximum range of the curve in FIG. 7 is caused by the series resonant circuit (R0, L0, C0) of the ultrasonic transducer. The minimum is located exactly at the resonant frequency ($f_r$). The curve to the left and right thereof is determined by the parallel resonant circuit.

Figure 8:
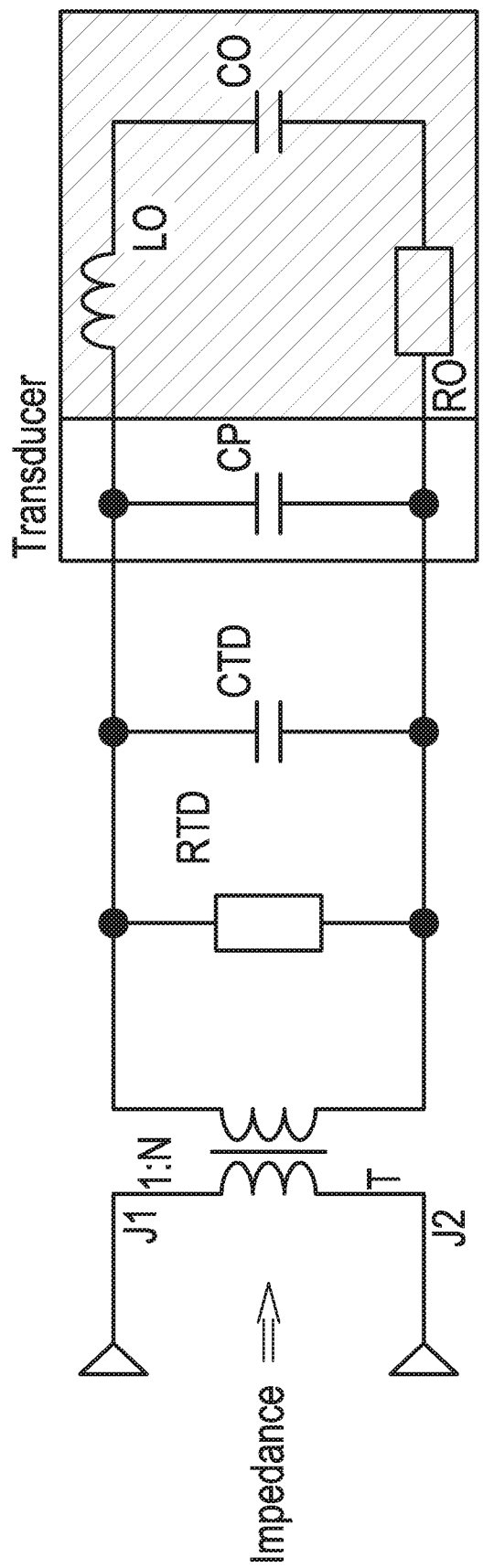
FIG. 8 shows a graphical representation of the changes of the equivalent circuit according to FIG. 6 for a simulation carried out to illustrate the disclosure.

To represent the influence of the series resonant circuit, a second simulation is carried out without series resonant circuit. The hatched regions in FIG. 8 of the equivalent circuit from FIG. 6 were removed for this simulation.

Figure 9:
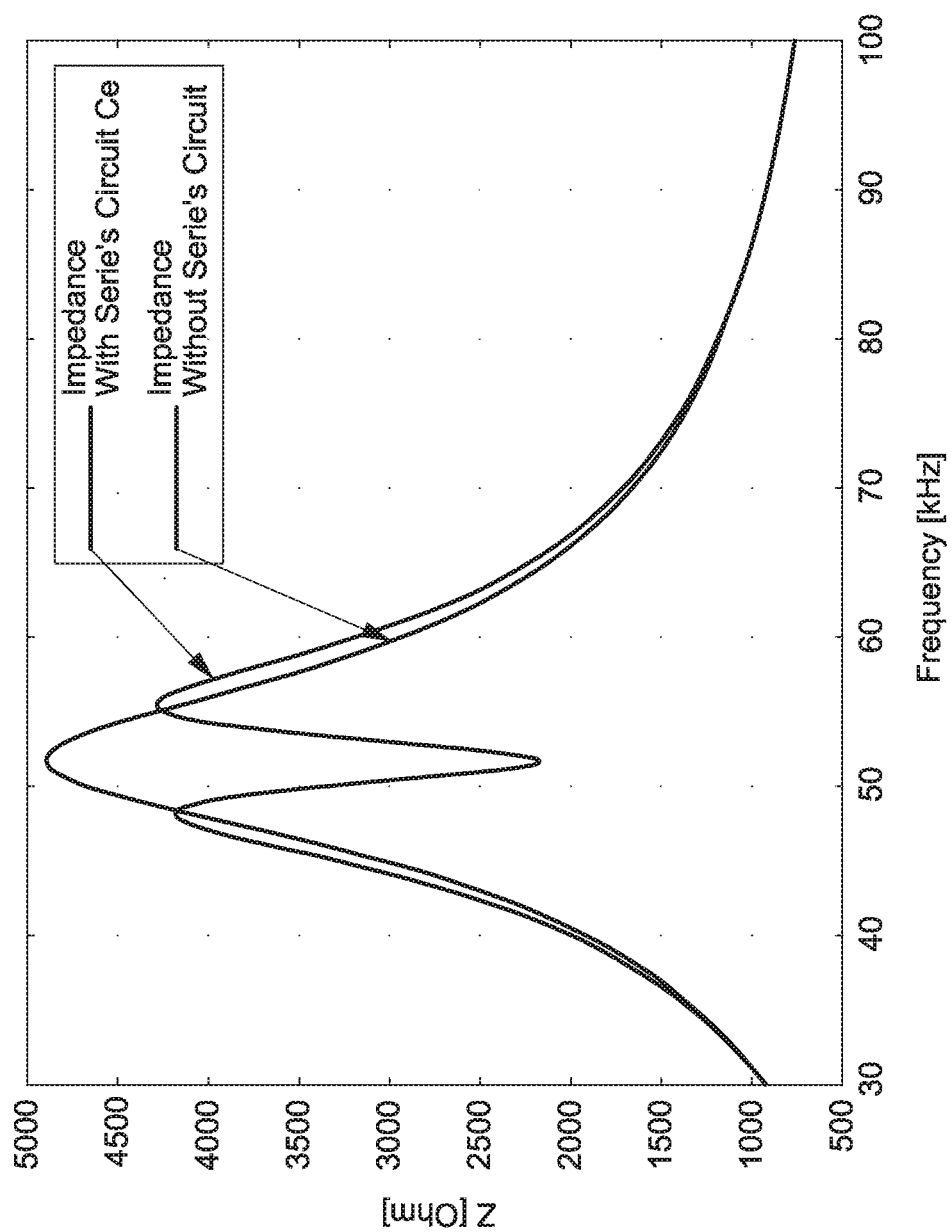
FIG. 9 shows the results of the simulations with changes to the equivalent circuit (see FIG. 8) and without changes to the equivalent circuit (see FIG. 6)

The result of the two simulations is shown in FIG. 9. It is apparent from FIG. 9 that the influence of the series resonant circuit can be neglected below a certain frequency (at approximately 40 kHz here) and above a certain frequency (at approximately 70 kHz here). This is a significant finding, which is disclosed and utilized here when it comes to operating the ultrasonic converter for the ascertainment of the vibrating element temperature at a measuring frequency that essentially deviates considerably to the upside or to the downside from the resonant frequency. In the frequency ranges on either side of the resonant frequency, the impedance is thus essentially determined by the parallel resonant circuit.

The following calculation shows that the transformer inductance is decisive for low frequencies, and the parallel capacitance is decisive in particular for high frequencies.

$$Z(\omega) = \frac{1}{\frac{1}{j\omega * LT} + \frac{1}{RTD} + j\omega(CTD + CP)}$$

For large values for $\omega$, it follows:

$$Z(\omega \gg \omega_g) = \frac{1}{j\omega(CTD + CP)}$$

where $$\omega_g = \frac{1}{\sqrt{LT(CTD + CP)}}$$

Figure 10:
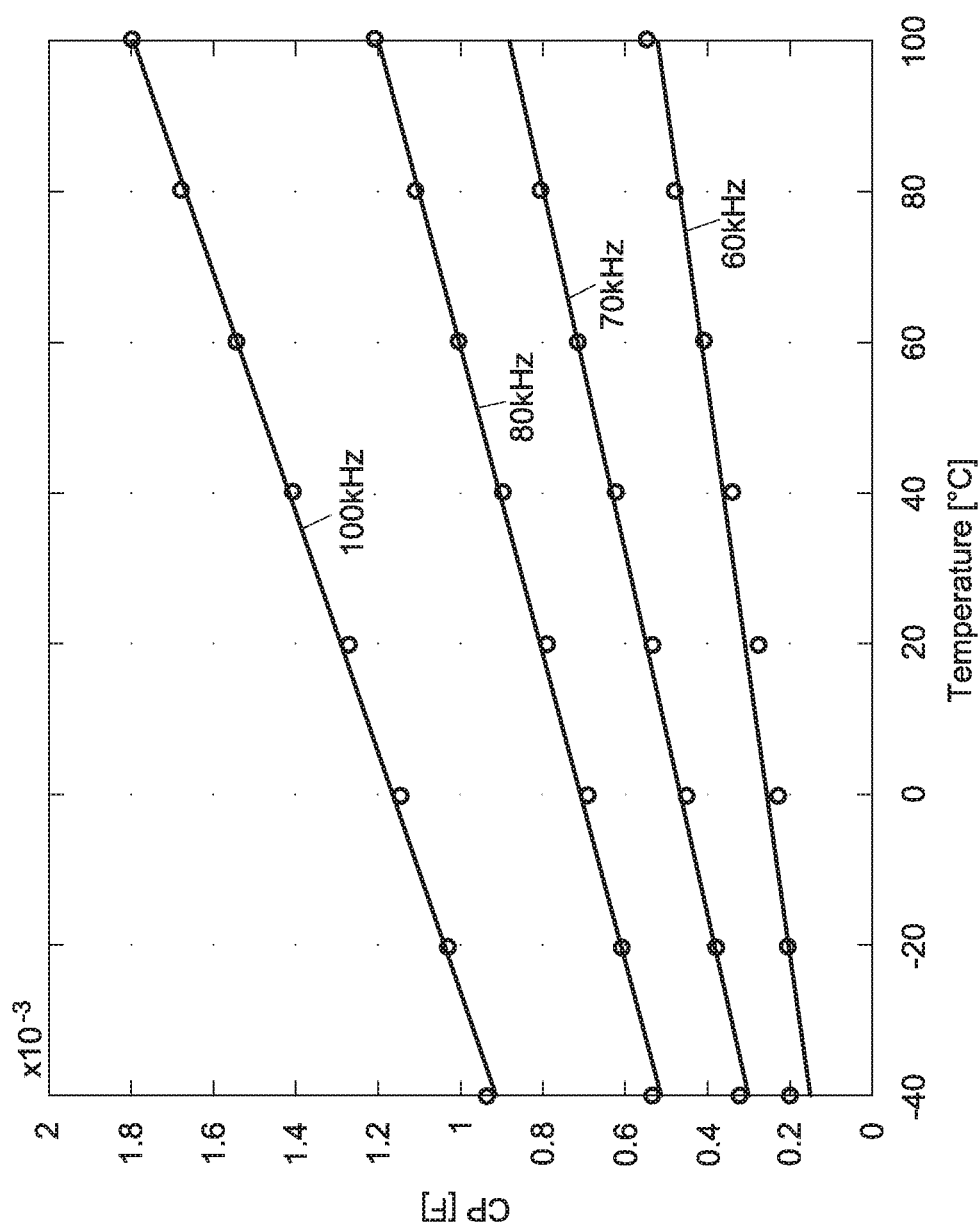
FIG. 10 shows the results of the impedance measurement of the ultrasonic converter at different measuring frequencies above the resonant frequency as a function of the temperature.

Plotting the reciprocal value of the impedance against the temperature in this frequency range yields a substantially linear relationship (see FIG. 10). FIG. 10 shows the results of an impedance measurement above the resonant frequency at different frequencies as a function of the temperature. The temperature-dependent elements of the series resonant circuit are taken into consideration.

In this way, the temperature can be ascertained by way of a linear map according to the formula $$\vartheta = \frac{1}{k(\omega)} Z(\omega) + \vartheta_0(\omega)$$

In this, $\vartheta$ denotes the temperature and $\omega$ the measuring frequency, $Z(\omega)$ denotes the ascertained absolute value of the complex impedance of the transducer at the measuring frequency ($\omega$) and $k(\omega)$ the slope at the measuring frequency, and $v_0(\omega)$ denotes the intercept at the measuring frequency ($\omega$). The values of the slope $k(\omega)$ and of the intercept $v_0(\omega)$ depend on the measuring frequency ($\omega$), as is apparent from FIG. 10. Moreover, these are transducer-specific and, in general, must be ascertained by way of experimentation.

Figure 11:
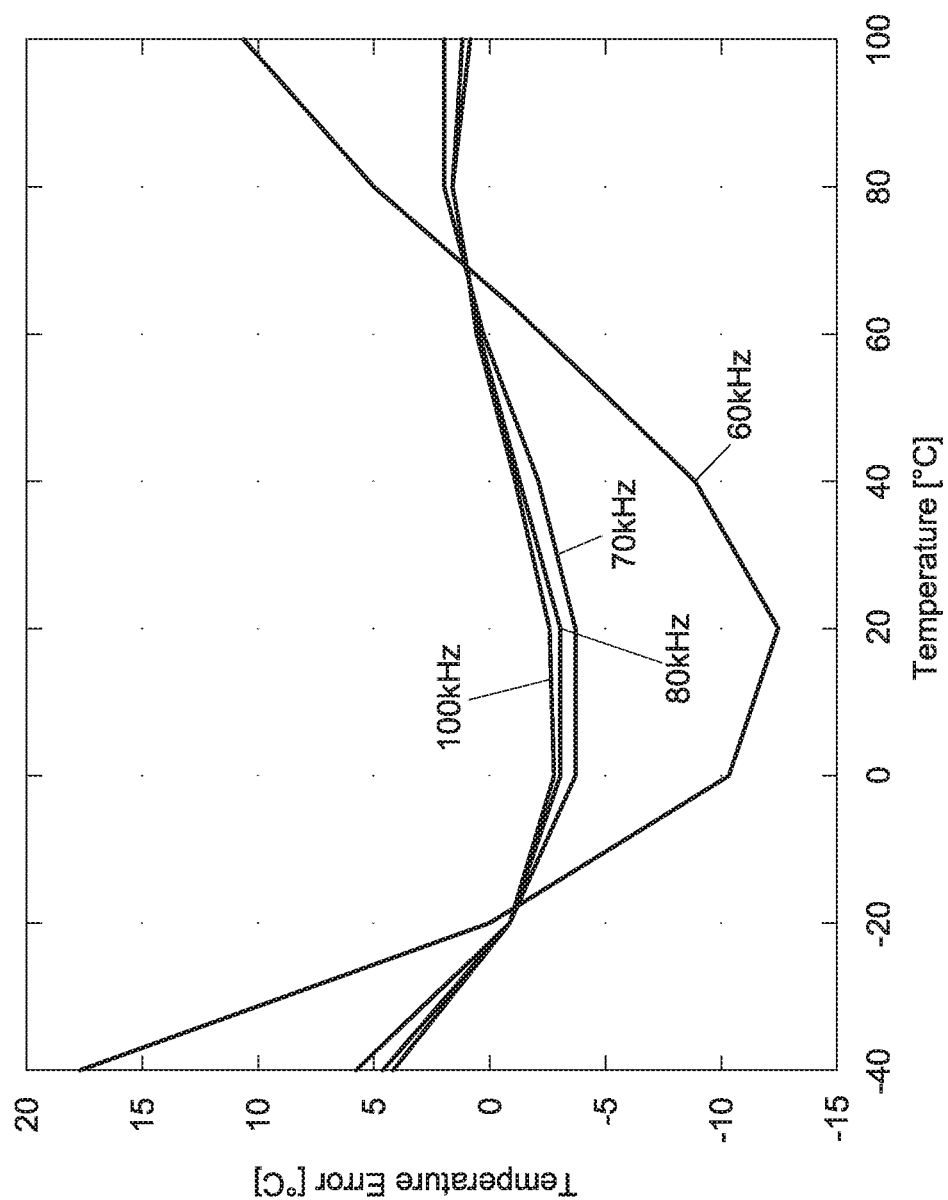
FIG. 11 shows the temperature errors as a function of the measuring frequency.

If the impedance measurement is now utilized to determine the temperature, temperature errors result as a function of the measuring frequency, as is shown in FIG. 11, assuming a linear relationship.

Figure 12:
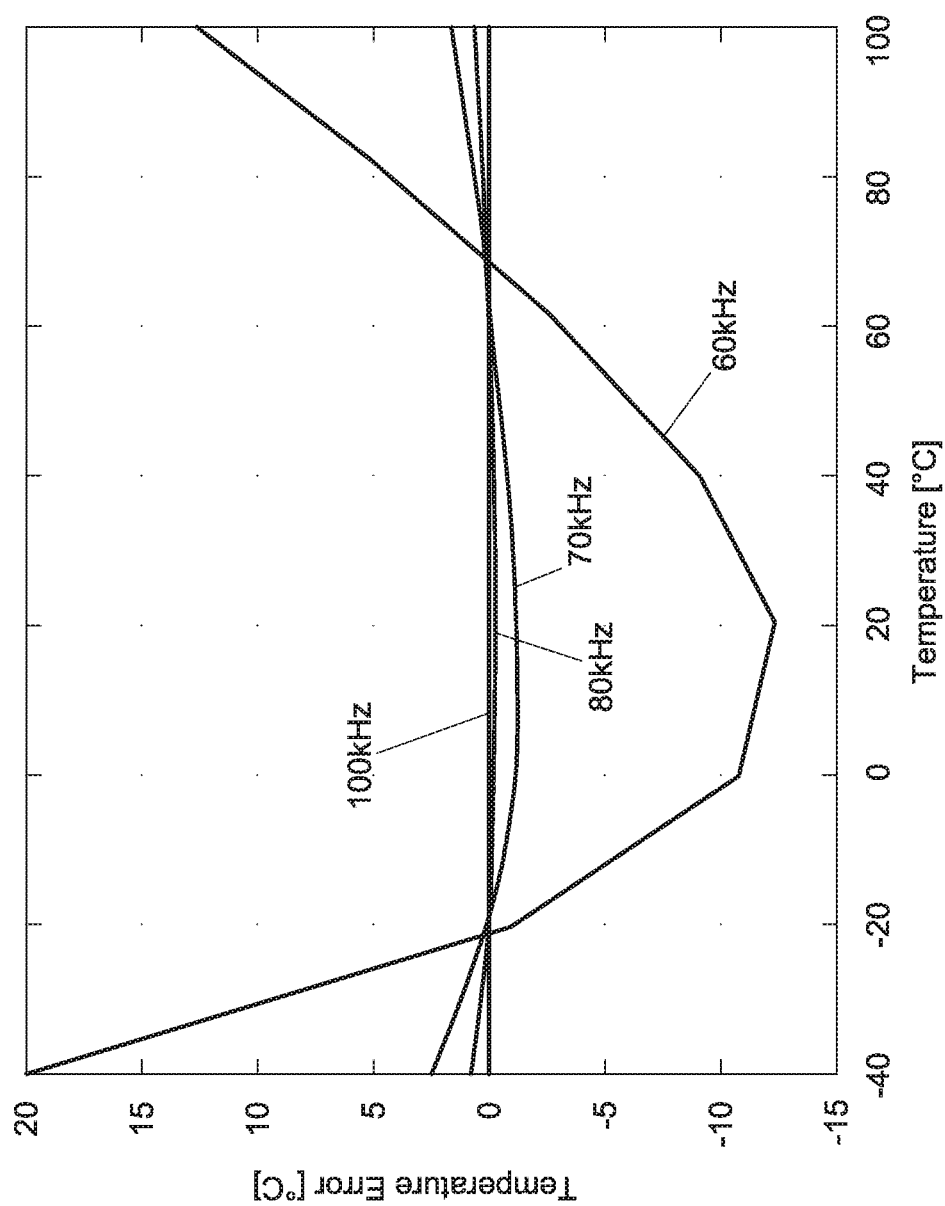
FIG. 12 shows the temperature error (1st degree polynomial) with a hypothetical linear response to temperature changes of the parallel capacitance (CP)

The more horizontal the lines extend, the lower is the error. Measurements above 70 kHz thus do not provide any significant improvement in accuracy. A closer look at FIG. 2 shows that the relationship between the temperature and capacitance is not strictly linear, but can be assumed to be linear with good approximation. If a linear response to temperature changes of the parallel capacitance (CP) is assumed in the simulation, the generally high precision of the method shown in FIG. 12 is obtained. FIG. 12 shows the temperature error (1st degree polynomial) with a hypothetical linear response to temperature changes of the parallel capacitance (CP).

Figure 13:
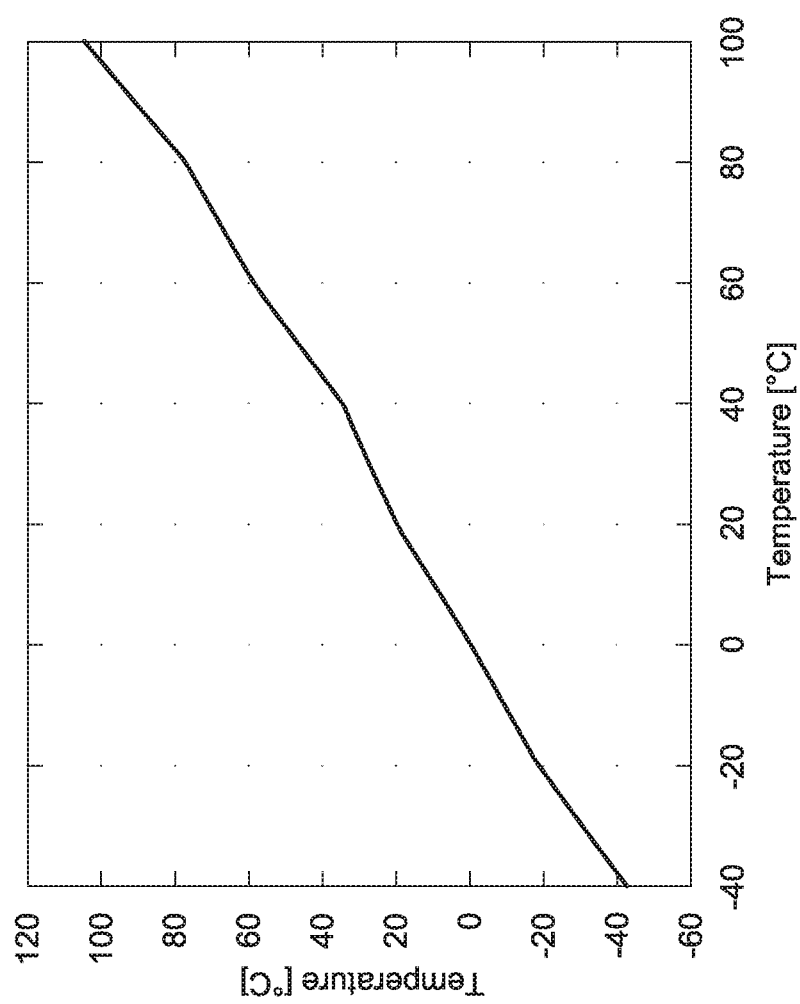
FIG. 13 shows exemplary measurement results.
Figure 14:
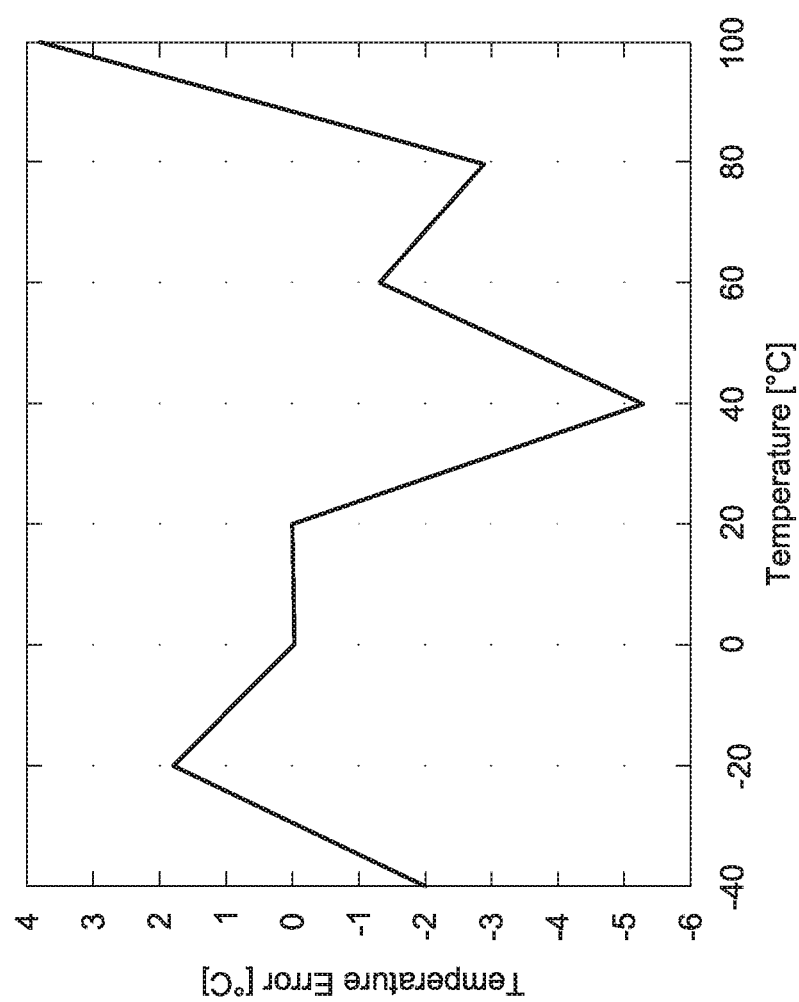
FIG. 14 shows the temperature measurement error associated with the measurement results from FIG. 13.

FIG. 13 shows exemplary measuring results, which were obtained in the above-described manner in a real set-up. The temperature is plotted on the X axis, and the temperature calculated in the manner described above is plotted on the Y axis. FIG. 14 shows the associated error. It is apparent that the temperature, in this example, can be measured approximately within +/−5° C. If necessary, statistical examinations, which are routine for a person skilled in the art, may need to be carried out here to ascertain the accuracy and the systematic errors.

Within the scope of the present disclosure, a method for detecting a value which represents the temperature of a vibrating element of an ultrasonic transducer is thus proposed. The ultrasonic transducer has a resonant frequency ($f_r$), as described above. In an example, the method comprises the step of operating the ultrasonic transducer with an electric measuring signal at a measuring frequency ($f_m$) which is above or below the resonant frequency ($f_r$) by at least a factor of 1.2 and/or better a factor of 1.3 and/or better by a factor of 1.4 and/or better by a factor of 1.5 and/or better by a factor of 1.6 and/or better by a factor of 1.7. As discussed above, it is typically sufficient to select the measuring frequency ($f_m$) to be 50% higher or lower than the resonant frequency (which is to say a factor of 1.5). During this operation, the step of detecting the absolute value of the complex impedance of ultrasonic transducer at this measuring frequency ($f_m$) is carried out. In this way, it becomes possible to ascertain the desired value, which is to represent the temperature of a vibrating element of an ultrasonic transducer, as a function of the detected absolute value of the complex impedance of the ultrasonic transducer at this measuring frequency ($f_m$). This ascertainment of the desired value, which is to represent the temperature of a vibrating element of an ultrasonic transducer, preferably takes place by a linear mapping of the detected absolute value of the complex impedance of the ultrasonic transducer. The parameters of this linear mapping can be ascertained during start-up of the device or during the initial start-up of a similar device or by simulation or calculation using data sheets of the ultrasonic transducers.

It is possible, of course, to carry out the above-described method by way of a suitable device. This is then a device for detecting a value which represents the temperature of a vibrating element of an ultrasonic transducer. In one example, this comprises an ultrasonic transducer, a measuring device and an evaluation device, which may be identical or equal to the measuring device. As was already described, the ultrasonic transducer has a resonant frequency ($f_r$). The measuring device is suitable or provided to operate the ultrasonic transducer at least intermittently with an electric measuring signal. It may be conceivable, for example, to use the driver device, which is provided for the normal operation of the ultrasonic transducer, and monitoring devices, which are used during operation of the ultrasonic transducer, as part of the measuring device for this measuring purpose at the time of the measurement. The measuring device is preferably configured and provided, for example, among other things, by the use of said driver stages, to operate the ultrasonic transducer at a measuring frequency ($f_m$) which is above or below the resonant frequency ($f_r$) of the ultrasonic transducer by at least a factor of 1.2 and/or better by a factor of 1.3 and/or better by a factor of 1.4 and/or better by a factor of 1.5 and/or better by a factor of 1.6 and/or better by a factor of 1.7. The measuring device is provided and suitable for detecting the absolute value of the complex impedance of the ultrasonic transducer at this measuring frequency ($f_m$). The evaluation device is suitable and provided for ascertaining and providing or for signaling the desired value, which is to represent the temperature of a vibrating element of an ultrasonic transducer, as a function of the detected absolute value of the complex impedance of the ultrasonic transducer at this measuring frequency ($f_m$). In particular, the evaluation device, for the ascertainment of the desired value, which is to represent the temperature of a vibrating element of an ultrasonic transducer, preferably carries out a linear mapping of the absolute value of the complex impedance of the ultrasonic transducer detected by the measuring device.

The particular advantage of the disclosure is the detection of the temperature of the ultrasonic converter itself without an additional sensor system, and only by operating the ultrasonic converter at a measuring frequency that is different from the resonant frequency, as described above, wherein the level of the impedance of the ultrasonic converter is used to ascertain the temperature. Faulty temperature ascertainments at other measuring sites having a lower temperature correlation with the temperature of the ultrasonic transducer vibrating element are avoided. The advantages, however, are not limited to these.

Exemplary implementations of the disclosure exhibit individual or all features of the respective following items or arbitrary combinations of the features of individual or multiple of the following items:

1. A method for detecting a value which represents the temperature of a vibrating element of an ultrasonic transducer, wherein the ultrasonic transducer has a resonant frequency ($f_r$), comprising the following steps:
    operating the ultrasonic transducer with an electric measuring signal (operating measuring voltage, for example) at a measuring frequency ($f_m$) which is above or below the resonant frequency ($f_r$) by at least a factor of 1.2 and/or a factor of 1.3 and/or by a factor of 1.4 and/or a factor of 1.5 and/or a factor of 1.6 and/or a factor of 1.7 of the same, which is to say is 1.2 times and/or 1.3 times and/or 1.4 times and/or 1.5 times and/or 1.6 times and/or 1.7 times or more the resonant frequency ($f_r$), or is $2/10$, $3/10$, $4/10$, $5/10$, $6/10$, $7/10$ or more of the resonant frequency ($f_r$) smaller than the same;
    detecting the absolute value of the complex impedance of the ultrasonic transducer at this measuring frequency ($f_m$) (for example, based on the operating measuring voltage);
    ascertaining the desired value, which is to represent the temperature of a vibrating element of an ultrasonic transducer, as a function of the detected absolute value of the complex impedance of the ultrasonic transducer at this measuring frequency ($f_m$).

2. The method according to item 1, wherein the ascertainment of the desired value, which is to represent the temperature of the vibrating element of the ultrasonic transducer, takes place by a linear mapping of the detected absolute value of the complex impedance of the ultrasonic transducer.

3. A device for detecting a value which represents the temperature of a vibrating element of an ultrasonic transducer, comprising:
    an ultrasonic transducer;
    a measuring device;
    an evaluation device, which may be part of the measuring device;
    the ultrasonic transducer having a resonant frequency ($f_r$);
    the measuring device being suitable to operate the ultrasonic transducer at least intermittently with an electric measuring signal (for example, operating measuring voltage); and
    the measuring device being configured to operate the ultrasonic transducer at a measuring frequency ($f_m$) which is above the resonant frequency ($f_r$) of the ultrasonic transducer by at least a factor of 1.2 and/or a factor of 1.3 and/or by a factor of 1.4 and/or a factor of 1.5 and/or a factor of 1.6 and/or a factor of 1.7, which is to say is 1.2 times and/or 1.3 times and/or 1.4 times and/or 1.5 times and/or 1.6 times and/or 1.7 times or more the resonant frequency ($f_r$), or is $2/10$, $3/10$, $4/10$, $5/10$, $6/10$, $7/10$ or more of the resonant frequency ($f_r$) smaller than the same;
    the measuring device being suitable for detecting the absolute value of the complex impedance of the ultrasonic transducer at this measuring frequency ($f_m$); and
    the evaluation device being suitable for ascertaining and providing or for signaling the desired value, which represents the temperature of a vibrating element of an ultrasonic transducer, as a function of the detected absolute value of the complex impedance of the ultrasonic transducer at this measuring frequency ($f_m$).

4. The device according to item 3, wherein the evaluation device, for the ascertainment of the desired value, which represents the temperature of the vibrating element of the ultrasonic transducer, carries out a linear mapping of the absolute value of the complex impedance of the ultrasonic transducer detected by the measuring device.

The invention claimed is:

1. A method for ascertaining a temperature of a vibrating element of an ultrasonic converter having a resonant frequency, the method comprising:
  operating the ultrasonic converter with a measuring signal having a frequency that is at least 0.2 times the resonant frequency greater or smaller than the resonant frequency;
  ascertaining a complex impedance of the ultrasonic converter upon activation by way of the measuring signal having the frequency, and determining an absolute value of the complex impedance; and
  ascertaining, based on a level of the absolute value of the complex impedance and the frequency of the measuring signal for operating the ultrasonic converter, the temperature of the vibrating element of the ultrasonic converter.

2. The method of claim 1, wherein the measuring signal has a frequency that is at least 0.3 times the resonant frequency greater or smaller than the resonant frequency.

3. The method of claim 1, wherein the measuring signal has a frequency that is at least 0.4 times the resonant frequency greater or smaller than the resonant frequency.

4. The method of claim 1, wherein the measuring signal has a frequency that is at least 0.5 times the resonant frequency greater or smaller than the resonant frequency.

5. The method of claim 1, wherein the measuring signal has a frequency that is at least 0.7 times the resonant frequency greater or smaller than the resonant frequency.

6. The method according to claim 1, further comprising: ascertaining the temperature of the vibrating element of the ultrasonic converter in a form of a value representing the temperature.

7. The method according to claim 1, wherein the vibrating element comprises a piezoelectric element.

8. The method according to claim 1, wherein a relationship between the temperature of the vibrating element and the level of the absolute value of the complex impedance of the ultrasonic converter is determined in advance of the operation of the ultrasonic converter with the measurement signal for ascertaining the temperature of the vibrating element of the ultrasonic converter, with the frequency of the measuring signal as a parameter, and the temperature of the vibrating element of the ultrasonic converter is ascertained with the aid of the relationship based on the level of the absolute value of the complex impedance and the frequency of the measuring signal during operation of the ultrasonic converter.

9. The method of claim 8, wherein the relationship between the temperature of the vibrating element and the level of the absolute value of the complex impedance of the ultrasonic converter is stored in a look-up table.

10. The method according to claim 8, wherein the relationship for any possible frequency of the measuring signal as the parameter is an essentially linear mapping of the reciprocal value of the level of the absolute value of the complex impedance of the ultrasonic converter against the temperature of the vibrating element.

11. Use of the method according to claim 1 for adapting a temperature-dependent propagation time of sound waves emitted by the ultrasonic converter to a current temperature of the vibrating element in connection with an ascertainment of a distance of an object reflecting the sound waves in a surrounding area of the ultrasonic converter.

12. Use of the method according to claim 1 for adapting a frequency of an operating signal of the ultrasonic converter for exciting the vibrating element of the ultrasonic converter at the resonant frequency.

13. A device for ascertaining a temperature of a vibrating element of an ultrasonic converter having a resonant frequency, comprising:
  a measuring device for providing a measuring signal for at least partially activating the ultrasonic converter with a frequency that is at least 0.2 times the resonant frequency greater or smaller than the resonant frequency;
  wherein a level of a complex impedance of the ultrasonic converter arising upon activation of the ultrasonic converter with the measuring signal having the frequency that is at least 0.2 times the resonant frequency greater or smaller than the resonant frequency, and an absolute value thereof, can be ascertained by way of the measuring device; and
  an evaluation unit for ascertaining the temperature of the vibrating element of the ultrasonic converter based on the level of the absolute value of the complex impedance and the frequency of the measuring signal.

14. The device according to claim 13, wherein the temperature of the vibrating element of the ultrasonic converter is ascertainable in the form of a value representing the temperature.

15. The device according to claim 13, wherein the vibrating element comprises a piezoelectric element.

16. The device according to claim 13, wherein a relationship between the temperature of the vibrating element and the level of the absolute value of the complex impedance of the ultrasonic converter is determined in advance of the activation of the ultrasonic converter with the measurement signal for ascertaining the temperature of the vibrating element of the ultrasonic converter, with the frequency of the measuring signal as a parameter, and the temperature of the vibrating element of the ultrasonic converter is ascertainable with the aid of the relationship based on the level of the absolute value of the complex impedance and the frequency of the measuring signal during operation of the ultrasonic converter.

17. The device of claim 16, wherein the relationship between the temperature of the vibrating element and the level of the absolute value of the complex impedance of the ultrasonic converter is stored in a look-up table of the evaluation unit.

18. The device according to claim 16, wherein the relationship for any possible frequency of the measuring signal as the parameter is an essentially linear mapping of a reciprocal value of the level of the absolute value of the complex impedance of the ultrasonic converter against the temperature of the vibrating element.

19. Use of the device according to claim 13 for adapting a temperature-dependent propagation time of sound waves emitted by the ultrasonic converter to a current temperature of the vibrating element in connection with an ascertainment of a distance of an object reflecting the sound waves in a surrounding area of the ultrasonic converter.

20. Use of the device according to claim 13 for adapting a frequency of an operating signal of the ultrasonic converter for exciting the vibrating element of the ultrasonic converter at the resonant frequency.

\* \* \* \* \*